(12) United States Patent
Carter et al.

(10) Patent No.: US 7,608,268 B2
(45) Date of Patent: *Oct. 27, 2009

(54) FERRITIN FUSION PROTEINS FOR USE IN VACCINES AND OTHER APPLICATIONS

(75) Inventors: Daniel C. Carter, Huntsville, AL (US); Chester Q. Li, Madison, AL (US)

(73) Assignee: New Century Pharmaceuticals, Inc., Huntsville, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/374,066

(22) Filed: Mar. 14, 2006

(65) Prior Publication Data

US 2006/0251679 A1 Nov. 9, 2006

Related U.S. Application Data

(63) Continuation of application No. 10/435,666, filed on May 12, 2003, now Pat. No. 7,097,841.

(60) Provisional application No. 60/379,145, filed on May 10, 2002.

(51) Int. Cl.
*A61K 39/12* (2006.01)
*A61K 39/395* (2006.01)
*C07K 19/00* (2006.01)
*C12N 15/62* (2006.01)

(52) U.S. Cl. ............ 424/192.1; 424/185.1; 424/186.1; 424/188.1; 424/221.1; 424/178.1; 424/134.4; 530/350; 530/400; 530/387.3; 514/2; 514/6; 536/23.4; 435/262

(58) Field of Classification Search .................. None
See application file for complete search history.

(56) References Cited

U.S. PATENT DOCUMENTS 7,097,841 B2 * 8/2006 Carter et al. ............ 424/192.1

OTHER PUBLICATIONS

Meola et at (Journal of Immunology 154: 3162-3172, 1995).*
Sidoli et al (Journal of Biological Chemistry 268:21819-21825, 1993).*
Kim et al (Biochemical and Biophysical Research Communications 289:125-129, 2001).*
Luzzago et al (EMBO Journal 8: 569-576, 1989).*
Von Darl et al (European Journal of Biochemistry 222:367-376, 1994).*
Harrison et al. Biochimica et Biophysica Acta 1275:161-203, 1996.*
Meola A. et al, "Derivation of vaccines from mimotopes: immunologic properties of human hepatitis B virus surface antigen mimotopes displayed on filamentous phage" 1995, pp. 3162-3172, vol. 154, No. 7, Journal of Immunology.

* cited by examiner

*Primary Examiner*—Mary E Mosher
(74) *Attorney, Agent, or Firm*—B. Aaron Schulman; Terry L. Wright; Stites & Harbison PLLC

(57) ABSTRACT

An isolated ferritin fusion protein is provided in which ferritin is fused with a protein or peptide capable of being fused to ferritin without interfering with the polymeric self-assembly of the resulting fusion protein, and the protein may be of the endocapsid form when fused at the C terminus or an exocapsid form when fused at the N terminus. These fusion proteins may self-assemble into a variety of useful higher polymeric forms, e.g., capsid or other polymeric aggregate, and they are advantageous in that they are useful in a variety of applications, including human and veterinary vaccines and therapeutics, blood substitutes, image contrast agents, metal chelating agents, gelling agents, protein purification platforms, and therapeutic receptor-binding proteins.

19 Claims, 10 Drawing Sheets

TEM OF Ag4-LLF (NCP PREP)

SEQUENCE LISTING

```
<160> NUMBER OF SEQ ID NOS: 8

<210> SEQ ID NO 1
<211> LENGTH: 12
<212> TYPE: PRT
<213> ORGANISM: Homo sapiens

<400> SEQUENCE: 1

Asn Pro Ser Ser Leu Phe Arg Tyr Leu Pro Ser Asp
1               5                   10

<210> SEQ ID NO 2
<211> LENGTH: 86
<212> TYPE: PRT
<213> ORGANISM: Homo sapiens
```

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 3
<211> LENGTH: 6
<212> TYPE: PRT
<213> ORGANISM: Homo sapiens

<400> SEQUENCE: 3

Gly Gly Gly Gly Gly Gly
1               5

<210> SEQ ID NO 4
<211> LENGTH: 175
<212> TYPE: PRT
<213> ORGANISM: Homo sapiens

<400> SEQUENCE: 4

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 5
<211> LENGTH: 9
<212> TYPE: PRT
<213> ORGANISM: Homo sapiens

<400> SEQUENCE: 5

Gln Pro Lys Thr Ala Cys Thr Asn Cys
1               5

<210> SEQ ID NO 6
<211> LENGTH: 231
<212> TYPE: PRT
<213> ORGANISM: Homo sapiens

<400> SEQUENCE: 6

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
                20                  25                  30

Ser Pro Glu Val Ile Pro Met Phe Ser Ala Leu Ser Glu Gly Ala Thr
            35                  40                  45

Pro Gln Asp Leu Asn Thr Met Leu Asn Thr Val Gly Gly His Gln Ala
        50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 7
<211> LENGTH: 142
<212> TYPE: PRT
<213> ORGANISM: Homo sapiens

<400> SEQUENCE: 7

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
                20                  25                  30

Met Phe Leu Ser Phe Pro Thr Thr Lys Thr Tyr Phe Pro His Phe Asp
            35                  40                  45

Leu Ser His Gly Ser Ala Gln Val Lys Gly His Gly Lys Lys Val Ala
        50                  55                  60

Asp Ala Leu Thr Asn Ala Val Ala His Val Asp Asp Met Pro Asn Ala

-continued

```
            65                  70                  75                  80
Leu Ser Ala Leu Ser Asp Leu His Ala His Lys Leu Arg Val Asp Pro
                85                  90                  95
Val Asn Phe Lys Leu Leu Ser His Cys Leu Leu Val Thr Leu Ala Ala
                100                 105                 110
His Leu Pro Ala Glu Phe Thr Pro Ala Val His Ala Ser Leu Asp Lys
                115                 120                 125
Phe Leu Ala Ser Val Ser Thr Val Leu Thr Ser Lys Tyr Arg
                130                 135                 140

<210> SEQ ID NO 8
<211> LENGTH: 190
<212> TYPE: PRT
<213> ORGANISM: Homo sapiens

<400> SEQUENCE: 8

Met Thr Thr Ala Ser Thr Ser Gln Val Arg Gln Asn Tyr His Gln Asp
1               5                   10                  15
Ser Glu Ala Ala Ile Asn Arg Gln Ile Asn Leu Glu Leu Tyr Ala Ser
                20                  25                  30
Tyr Val Tyr Leu Ser Met Ser Tyr Tyr Phe Asp Arg Asp Asp Val Ala
                35                  40                  45
Leu Lys Asn Phe Ala Lys Tyr Phe Leu His Gln Ser His Glu Glu Arg
        50                  55                  60
Glu His Ala Glu Lys Leu Met Lys Leu Gln Asn Gln Arg Gly Gly Arg
65                  70                  75                  80
Ile Phe Leu Gln Asp Ile Lys Lys Pro Asp Cys Asp Asp Trp Glu Ser
                85                  90                  95
Gly Leu Asn Ala Met Glu Cys Ala Leu His Leu Glu Lys Asn Val Asn
                100                 105                 110
Gln Ser Leu Leu Glu Leu His Lys Leu Ala Thr Asp Lys Asn Asp Pro
                115                 120                 125
His Leu Cys Asp Phe Ile Glu Thr His Tyr Leu Asn Glu Gln Val Lys
                130                 135                 140
Ala Ile Lys Glu Leu Gly Asp His Val Thr Asn Leu Arg Lys Met Gly
145                 150                 155                 160
Ala Pro Glu Ser Gly Leu Ala Glu Tyr Leu Phe Asp Lys His Thr Trp
                165                 170                 175
Glu Thr Val Ile Met Lys Ala Lys Pro Arg Ala Asn Phe Pro
                180                 185                 190
```

FERRITIN FUSION PROTEINS FOR USE IN VACCINES AND OTHER APPLICATIONS

CROSS-REFERENCE TO RELATED APPLICATIONS

The present application is a continuation application of U.S. patent application Ser. No. 10/435,666, filed May 12, 2003, now U.S. Pat. No. 7,097,841 which claimed the benefit of U.S. provisional application 60/379,145, filed May 10, 2002, incorporated herein by reference.

FIELD OF THE INVENTION

The present invention relates in general to ferritin fusion proteins, and in particular to the fusion of additional protein or peptide segments to either or both of the N and C termini, respectively, at the inner and outer surface of the ferritin protein to form a fusion protein capable of self-assembly, and to the use of such fusion proteins as vaccines and in other applications including oxygen transport and the therapeutic delivery of drugs and other therapeutic agents,

BACKGROUND OF THE INVENTION

Ferritin is a highly conserved 24 subunit protein that found in all animals, bacteria, and plants. The major physiological function of ferritin is to control the rate and location of polynuclear $Fe(III)_2O_3$ formation (see, e.g., Theil, E. C. "The ferritin family of iron storage proteins," Adv. Enzymol. Relat. Areas Mol. Biol. 63:421-449 (1990), and Harrison, P. M., Lilley, T. H. "Ferritin in Iron Carriers and Iron Proteins," Loehr T. M., ed. Weinheim: VCH, 1990:353-452; these and all references cited in the present application are incorporated herein by reference). This control is achieved through biomineralization which is performed by transporting hydrated iron ions and protons to and from a mineralized core. Through this mechanism, ferritin accumulates iron at concentrations orders of magnitude greater than the solubility of free iron under physiological conditions. The rate of biomineralization is directly related to the ratio of ferritin H and L subunits (the so-called heavy and light chains) within each capsid and exhibits the general trend of increasing the rate of iron storage with increasing H chain content. These differences in capsid composition are tissue dependent and affect the mechanism of iron oxidation, core formation and iron turnover. For example, ferritin comprised of predominantly L chain is found in the serum, while ferritin from the heart has a high ferritin H content. The ferritin mineralized iron core acts to provide bioavailable iron to a variety of redox enzymes and also serves a detoxification role.

Each ferritin protein is in the form of a 24 subunit capsid having 432 symmetry, a diameter of 125 Å, a shell thickness of approximately 25 Å and a hollow inner core of approximately 80 Å in diameter (FIG. 1). The monomeric ferritin typically has at least two isoforms denoted the L and H chains which differ in amino acid sequence. Although multiple forms of H and L subunit lengths have been identified in many vertebrates including humans, these two forms are generally both found in the ferritins that have been identified. Each ferritin subunit is approximately a 17 kilodalton protein having the topology of a helix bundle which includes a four-antiparallel helix motif, with a fifth shorter helix (the C-terminal helix) lying roughly perpendicular to the long axis of the 4 helix bundle. The helices are according to convention labeled 'A, B, C, D & E' from the N-terminus respectively.

The N-terminal sequence lies adjacent to the capsid three-fold axis and clearly extends to the surface, while the E helices pack together at the four-fold axis with the C-terminus extending into the capsid core. The consequence of this packing creates two pores on the capsid surface. The pore at the four-fold is approximately 4 to 5 Å across and predominantly hydrophobic, while the three-fold pore, being slightly larger at 6.0 Å diameter is predominantly hydrophilic. It is expected that one or both of these pores represent the point by which the hydrated iron diffuses into and out of the capsid.

Previous work on ferritins, such as disclosed in U.S. Pat. Nos. 5,248,589; 5,358,722; and 5,304,382, all incorporated herein by reference, has focused on the physical aspects of the protein shell and the core such that materials other than ferrihydrate may be located inside the shell. It has also been shown (S P Martsev, A P Vlasov, P Arosio, Protein Engineering vol. 11, 377-381 (1998)) that recombinant human L and H ferritin when explored by differential scanning calorimetry will dissociate into subunit monomers at pH 2.0 to 2.8.

Other recent works have involved the use of "virus-like" particles as a modular system for vaccines wherein antibody responses were induced in the absence of adjuvants resulting in protection from viral infection and allergic reactions (Lechner et al., Intervirology 2002; 45(4-6); 212-7), but this system did not involved a ferritin-based development of proteins. In Marchenko et al., J. Mol. Microbiol Biotechnol 2003; 5(2):97-104, virus-like particles (VLPs) were constructed from a protein known as P1-380 which forms VLPs. In this case, fusion at the C and/or N-termini of the P1-380 protein did not interfere with the VLP self-assembly, and bi-functional fusion particles were made which demonstrated that they are more potent at generating and immune response. Still further, Douglas et al. have performed some work wherein a protein for the nucleation of iron was linked with the cowpea mosaic virus (CCMV), See Adv. Mater., 14 (6): 415-418 (2002). Still other references refer to a "chimeric" protein using a virus-like particle which contains a nonstructural papillomavirus protein fused to the virus L2, a minor capsid protein. See Greenstone et al., PNAS USA, 95(4): 1800-5 (1998). However, in all of these cases, these fusion proteins did not involve ferritin.

Accordingly, none of the prior references have focused on utilizing ferritin or the placement of the N and C-termini at the outer and inner surface of the capsid respectively (e.g., as shown in FIGS. 2A & B, and described further below) for any purpose, and moreover, no one has previously has utilized this structure for the purpose of linking suitable proteins or peptides via fusion to ferritin in order to enhance the properties of the proteins or peptides while creating a fusion protein capable of self-assembly.

SUMMARY OF THE INVENTION

Accordingly, it is an object of the present invention to provide ferritin fusion proteins which comprise proteins or peptide segments contiguously fused to ferritin, such at either or both of the N and C termini.

It is further an object of the present invention to provide ferritin-fusion proteins further providing for a means to express proteins which may be either incorporated onto the surface of the capsid, or internalized through the extension of either terminus.

It is still further an object of the present invention to provide protein fusion products which can be used in such applications as vaccines, therapeutics, image contrast agents, novel metal chelating systems, gelling agents, protein purification platforms, therapeutic receptor-binding proteins, and other suitable applications.

It is even further an object of the present invention to provide ferritin fusion proteins which can be used in human and veterinary applications as well as numerous non therapeutic applications.

It is another object of the present invention to provide ferritin fusion proteins with increased vascular residence times so as to improve the likelihood of an immune response and provide prolonged therapeutic benefits from drugs and other therapeutic agents.

It is yet another object of the present invention to provide recombinant ferritin fusion proteins for use in vaccines, drug delivery, and many other therapeutic methods involving proteins and peptide segments which can be fused to ferritin without interfering with the ability of the protein for self-assembly or the ability to form higher polymeric assemblies, such as a capsid structure or a polymeric aggregate.

These and other objects are provided by virtue of the present invention which comprises a ferritin protein fused with a protein or peptide that can be expressed genetically along with the ferritin and which can allow the formation of the polymeric assembly of the ferritin, such as a ferritin capsid or other polymeric aggregate, in which the protein or peptide is linked with the N or C terminal region of the ferritin. The proteins or peptides will thus be used which do not restrict the self-assembly of the resulting fusion protein into useful higher polymeric forms, e.g., the capsid form, but other polymeric forms such as hemispherical shape, cylindrical, etc., are also possible. In accordance with the invention, the ferritin-fusion proteins provide a means to express proteins which may be either incorporated onto the outer portion of the ferritin, e.g., on the surface of the capsid, or internalized through the extension of either terminus. The advantages of the fusion proteins of the invention are manifold in that they can include viral envelope and capsid proteins so as to be utilized as viral vaccines, and because it is possible to have multiple proteins and peptides incorporated into the fusion protein of the invention, it is possible to construct multivalent fusion proteins, that can act as multivalent vaccines, containing different proteins from the same organism, or proteins from different organisms.

In addition, when formed into the ferritin capsid structure in which the C-terminal region is located at the inner core of the ferritin protein and the N-terminal region is located at the outer surface of the protein, it will be possible to construct vaccines wherein one type of protein or peptide antigen is located on the surface of the ferritin and will rapidly generate antibodies, but a second desired antigen can be linked at the internal C-terminal region and thus shield this antigen from initial immunogenic reaction for an extended period of time. The vaccine will thus have an initial portion that generates an initial set of antibodies, and will have a second portion which becomes immunogenic only after sufficient time has elapsed and the second antigen is exposed following dissociation of the ferritin core. Such internal shielding can provide a means to present non-aqueous soluble antigens. Even further, because the linkage with ferritin will enhance the useful lifetime of the protein or peptide before it is degraded, the fusion proteins of the invention will be useful in extending the useful life and beneficial effect of therapeutic proteins and peptides. Still other benefits possible by virtue of the fusion proteins of the invention is the use of the human capsid (or animal capsid in veterinary applications) to avoid immune-related problems when it is desired to make the linked peptide or protein be less likely to generate an immune response. A further example is the use of the ferritin capsid to assemble human hemoglobin polymers for use as potential oxygen transporting blood substitutes. Finally, such fusion proteins may also be beneficial in other ways, such as in metal scavenging, encapsulating beneficial proteins or small molecules, or storing radioactive materials that may be combined with antibodies and be targeted to a specific set of tissues or cells.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

FIG. 1 is a ribbon diagram of ferritin capsid as viewed in the direction of the 4-fold axis (center). Subunits shown in alternating colors.

FIGS. 2A-2B show stereoviews illustrating the view of ⅓ of the ferritin capsid down a four-fold axis (center). The exterior N-terminus and interior C-terminus are labeled clearly showing the availability of the termini for the creation of recombinant fusion peptides or proteins. FIG. 2A shows the view from inside the capsid, and FIG. 2B the view from the exterior surface.

Figure 5:
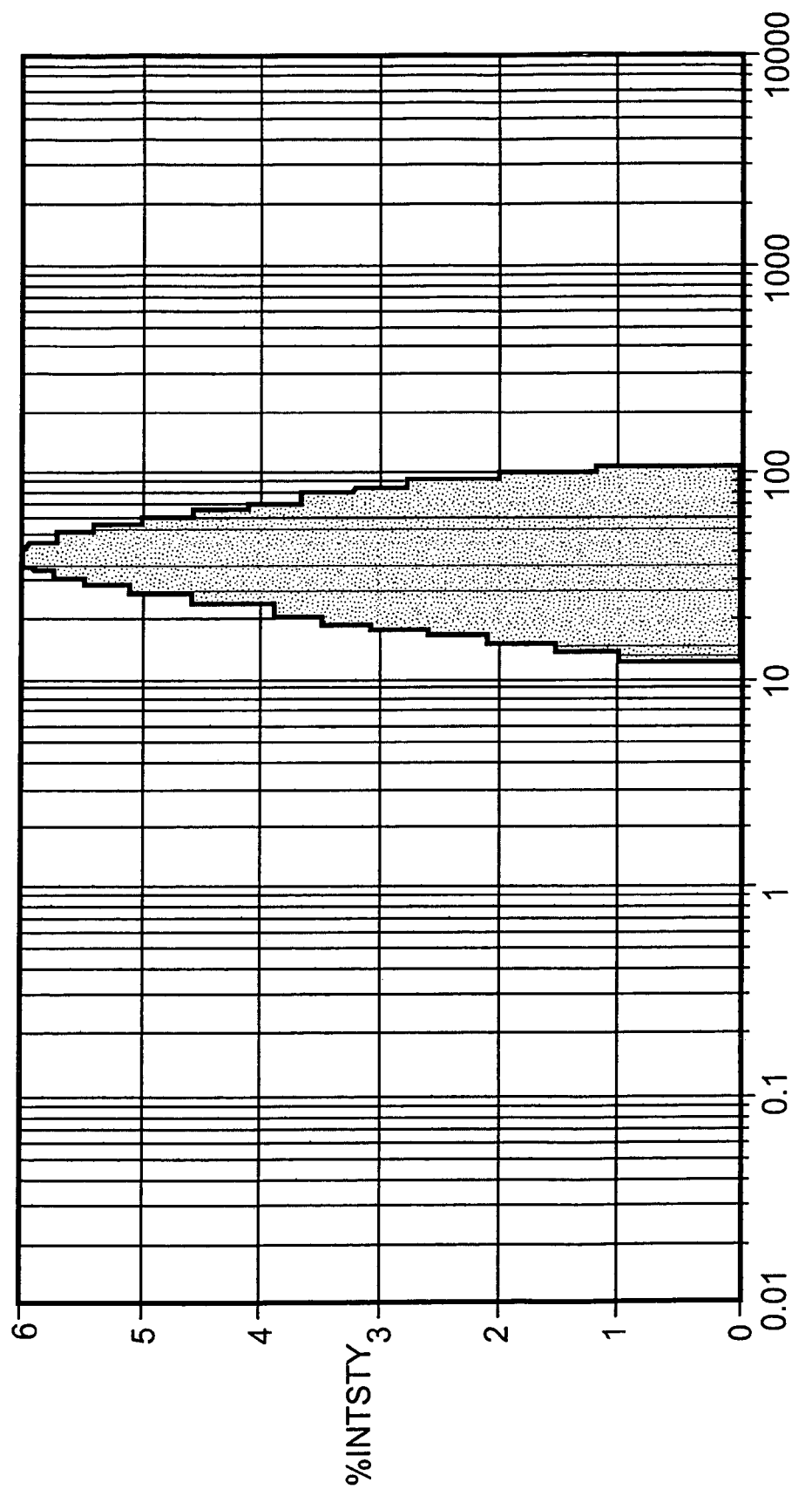

FIG. 5 illustrates the regularization histogram of ($F_L$. G. Hα).

Figure 6:
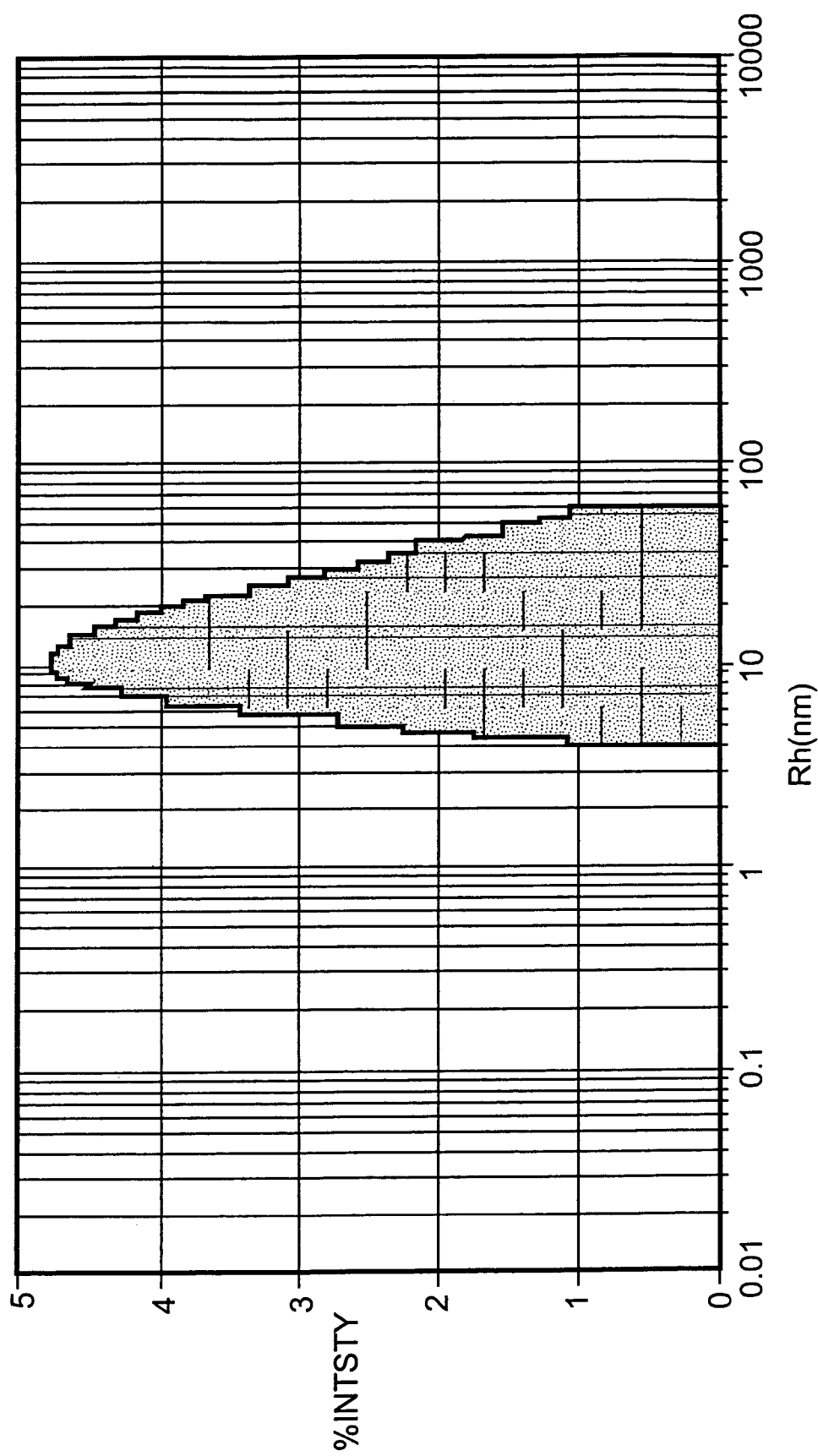

FIG. 6 illustrates the regularization histogram of native horse heart ferritin.

Figure 7:
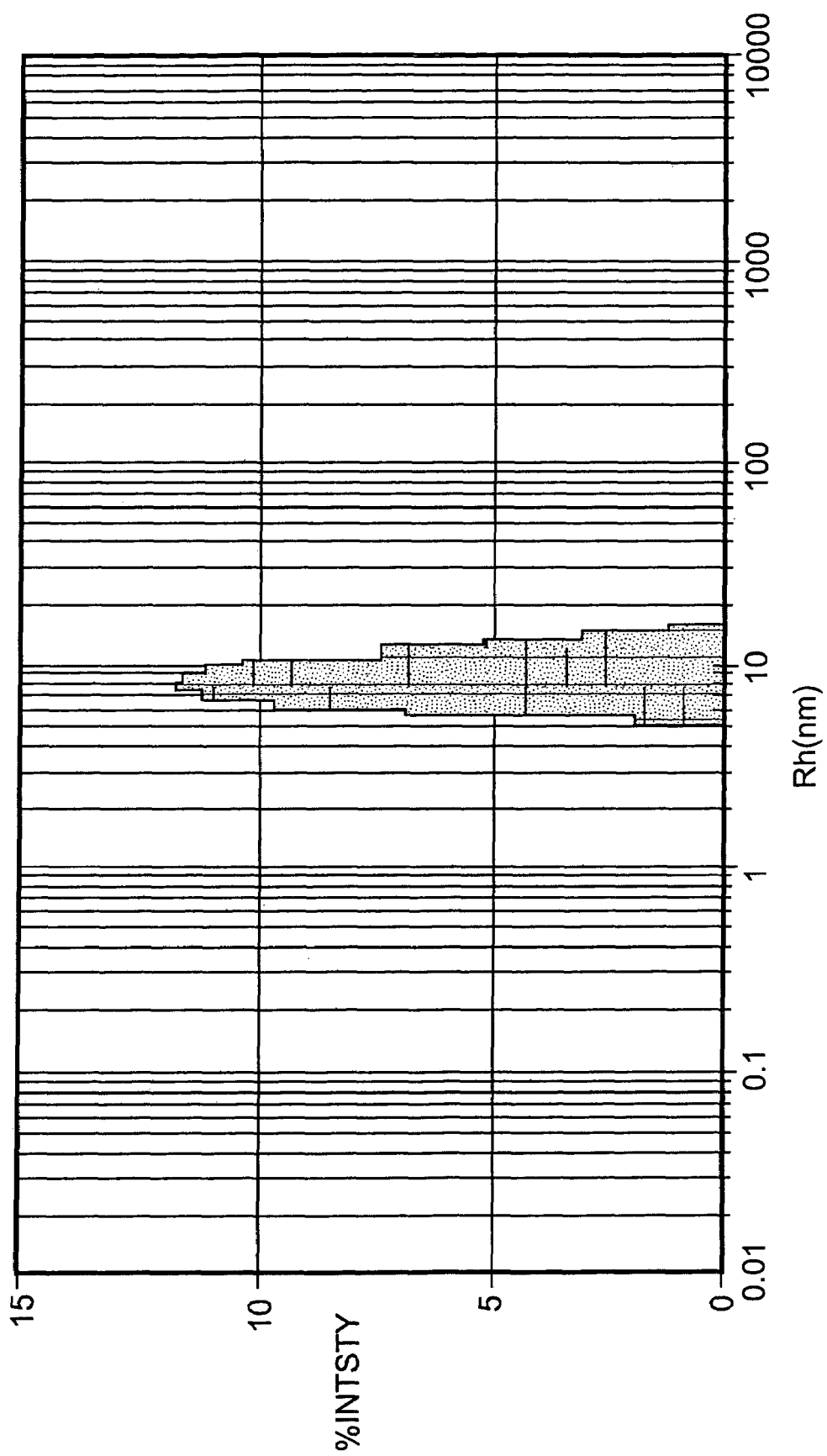

FIG. 7 illustrates the regularization histogram of ($F_L$. GG. Ag4).

Figure 8:
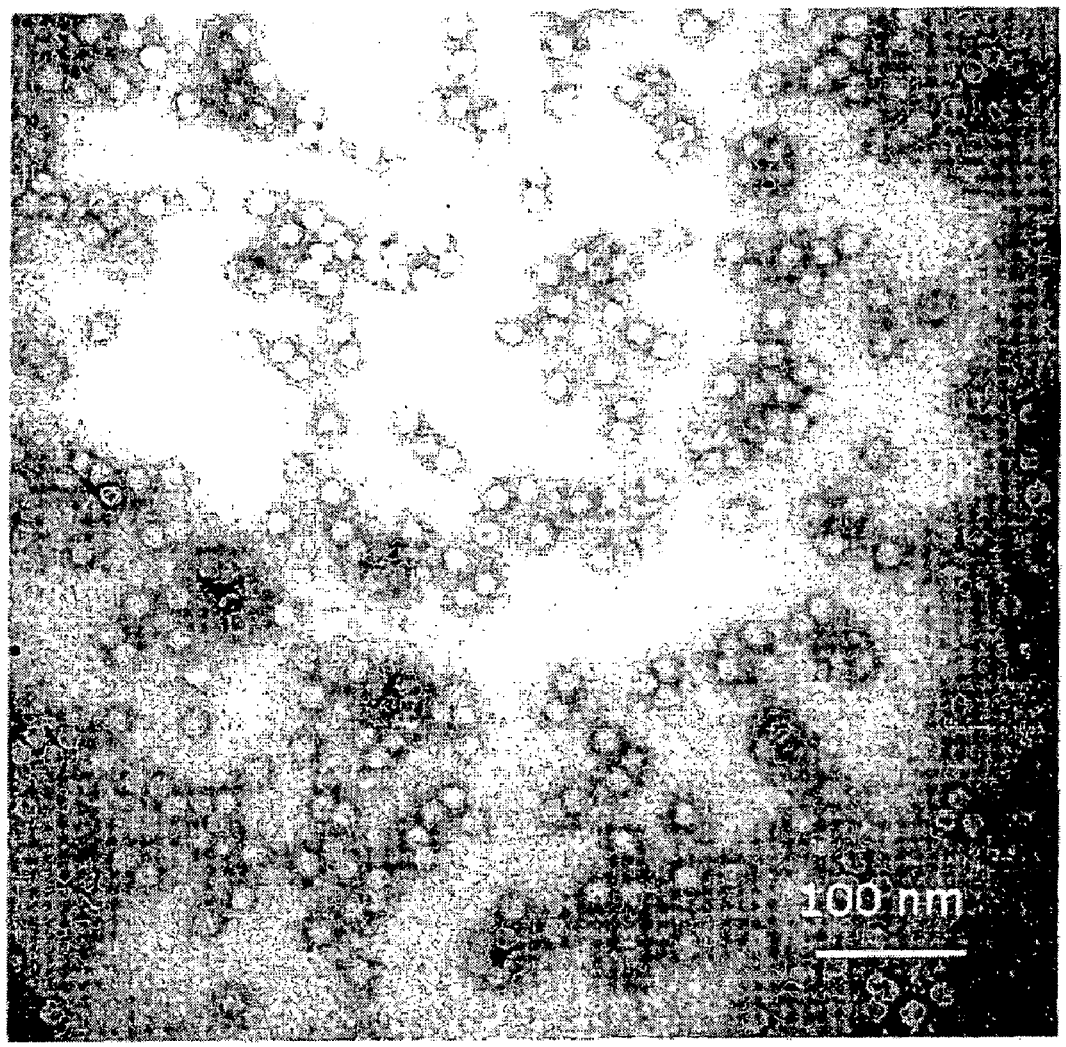

FIG. 8 is a transmission electron microscopy picture showing the proper capsid formation of ($F_L$. GG. Ag4).

Figure 9:
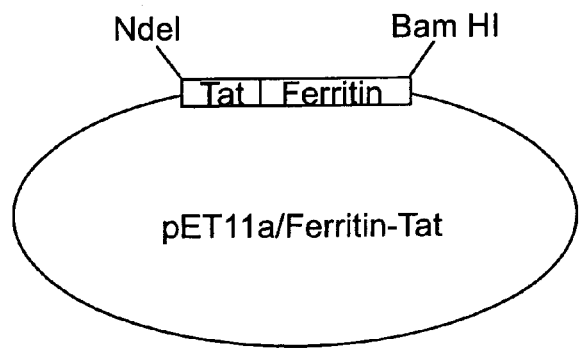

FIG. 9 is a schematic view of the plasmid coding for the fusion protein of HIV Tat protein (84 mer) to the human ferritin N-terminus in accordance with the invention.

Figure 10:
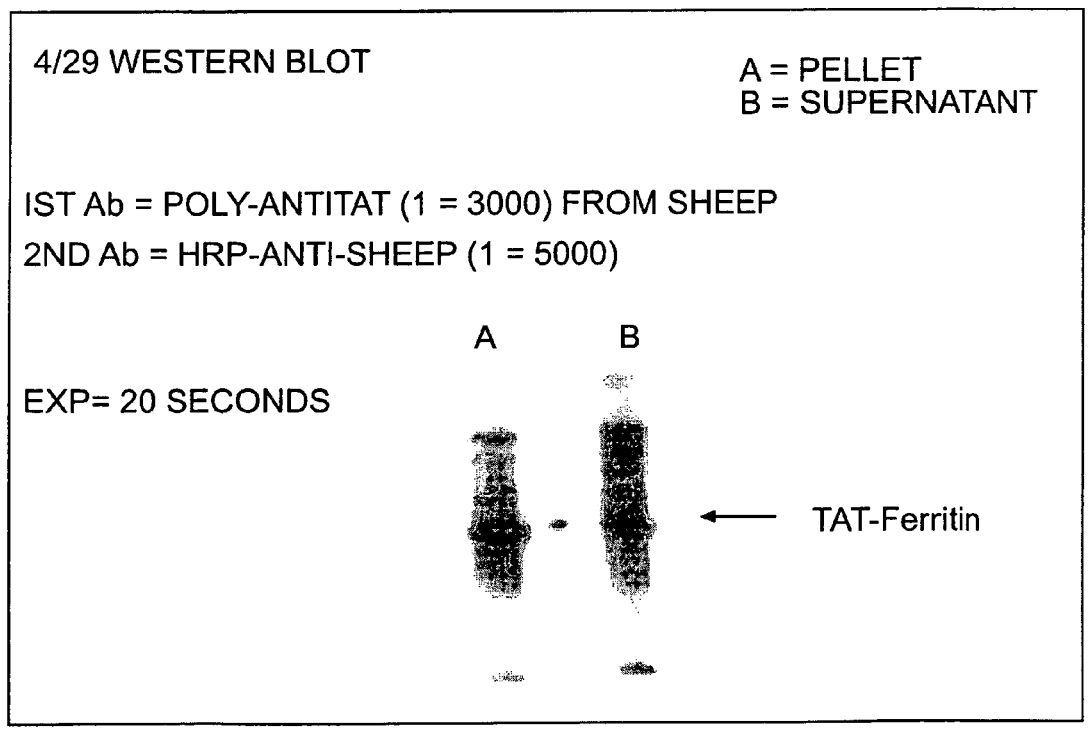
Figure 11:
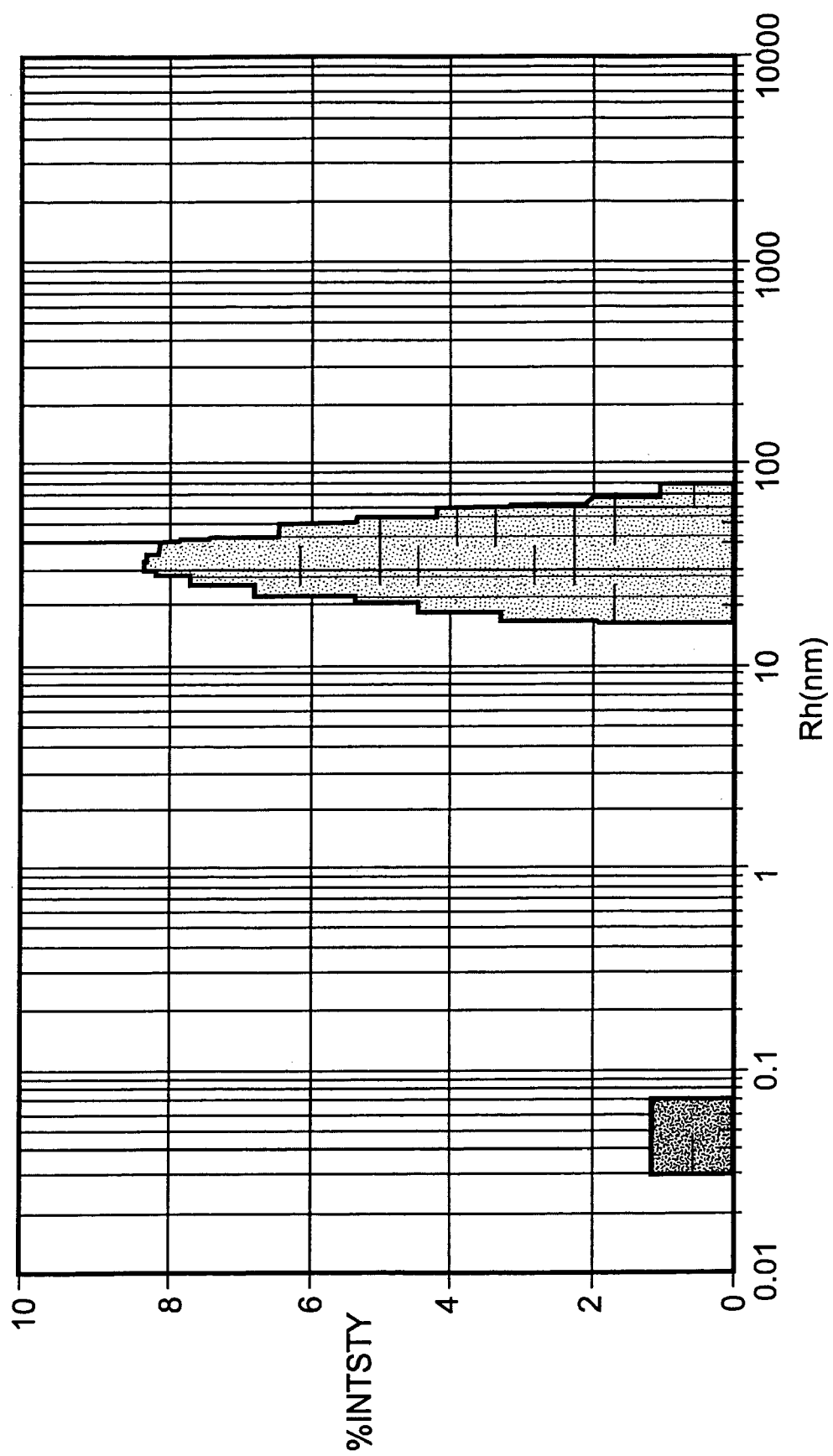

FIG. 10 shows the Western blot analysis using polyclonal antibodies to Tat which positively identified the ferritin-Tat fusion protein of the present invention FIG. 11 illustrates the regularization histogram of (Tat.6G.$F_L$).

Figure 12A:
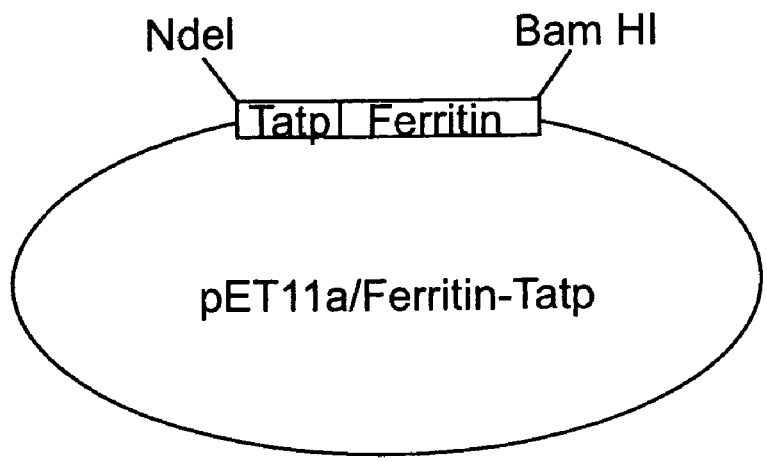

FIG. 12A is a schematic view of the plasmid coding for the fusion protein of a small HIV Tat peptide to the human ferritin light chain N-terminus in accordance with the invention.

Figure 12B:
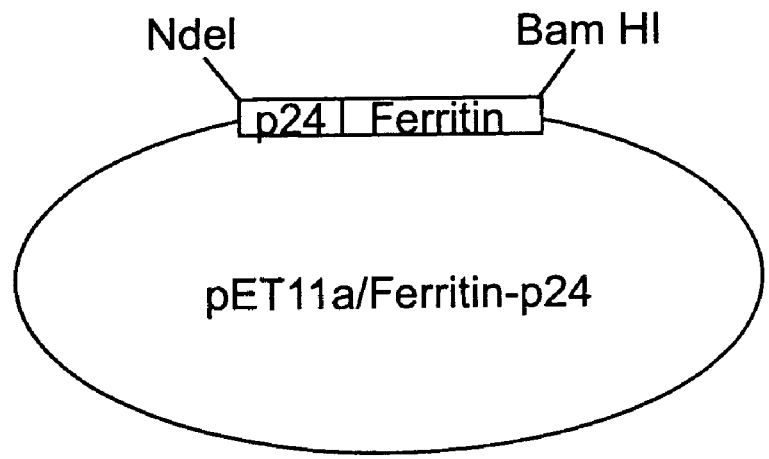

FIG. 12B is a schematic view of the plasmid coding for the fusion protein of the HIV P24 protein to the human ferritin light chain N-terminus in accordance with the invention.

DETAILED DESCRIPTION OF THE PREFERRED EMBODIMENTS

In accordance with the present invention, there are provided ferritin fusion proteins which comprise a fusion product between at least one chain of ferritin, such as the H or L chain, with a protein or peptide capable of binding at the N terminus or C terminus of ferritin yet which does not interfere with the ability of the resulting fusion protein to form a polymeric assembly, such as a capsid, a polymeric aggregate, or other functional shape. Ferritin is a highly conserved 24 subunit protein that is found in all animals, bacteria, and plants which acts primarily to control the rate and location of polynuclear $Fe(III)_2O_3$ formation through the transportation of hydrated iron ions and protons to and from a mineralized core. Through this mechanism, ferritin accumulates iron at concentrations orders of magnitude greater than the solubility of free iron under physiological conditions. The rate of biomineralization is directly related to the ratio of ferritin H and L subunits (the so-called heavy and light chains) within each capsid and exhibits the general trend of increasing the rate of iron storage with increasing H chain content. These differences in capsid composition are tissue dependent and affect the mechanism of iron oxidation, core formation and iron turnover. The ferritin mineralized iron core acts to provide bioavailable iron to a variety of redox enzymes and also serves a detoxification role.

Figure 1:
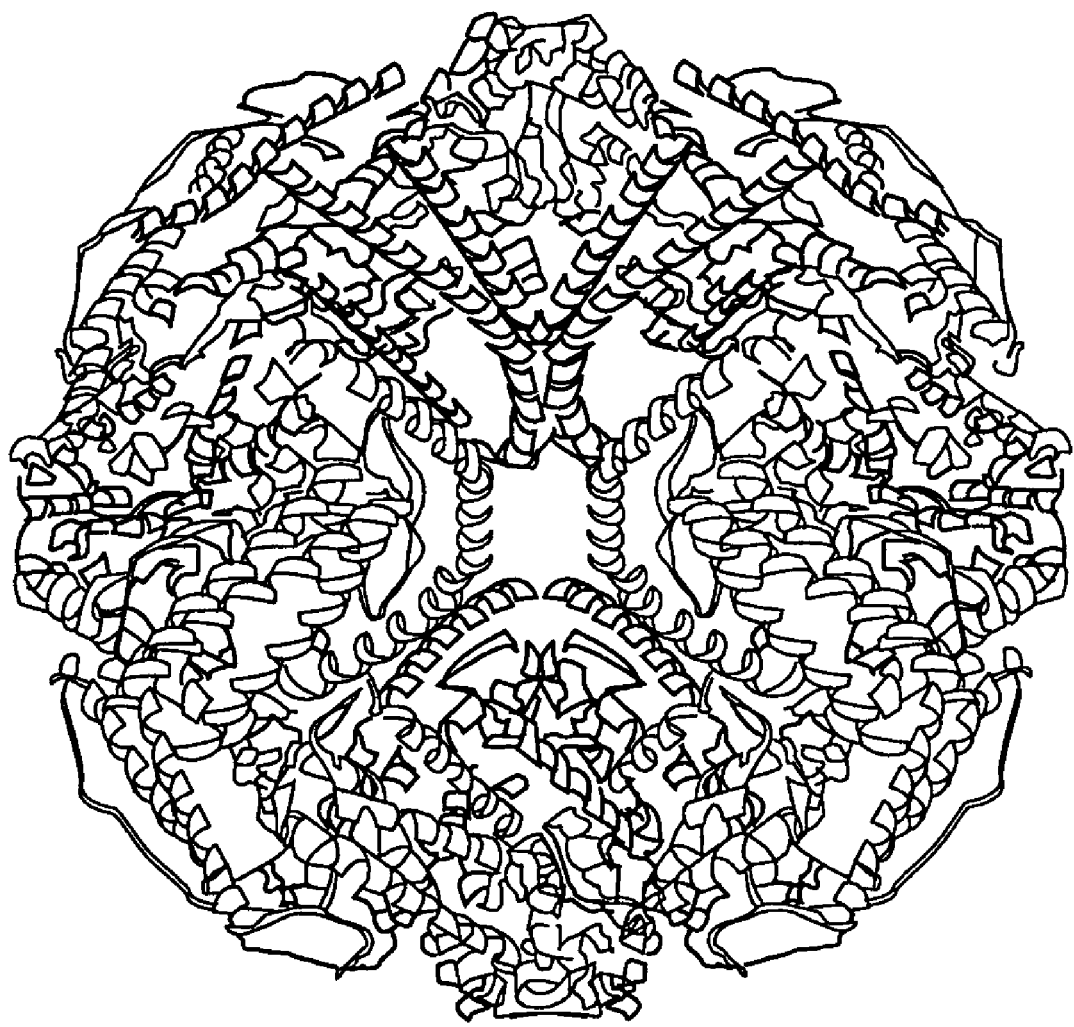

Each ferritin protein is in the form of a 24 subunit capsid having 432 symmetry, a diameter of 125 Å, a shell thickness of approximately 25 Å and a hollow inner core of approximately 80 Å in diameter (FIG. 1). The monomeric ferritin typically has at least two isoforms denoted the L and H chains which differ in amino acid sequence, and multiple forms of H and L subunit lengths have been identified in many vertebrates including humans. Each ferritin subunit is approximately a 17 kilodalton protein having the topology of a helix bundle which includes a four antiparallel helix motif, with a fifth shorter helix (the c-terminal helix) lying roughly perpendicular to the long axis of the 4 helix bundle. The helices are according to convention labeled 'A, B, C, D & E' from the N-terminus respectively. The N-terminal sequence lies adjacent to the capsid three-fold axis and clearly extends to the surface, while the E helices pack together at the four-fold axis with the C-terminus extending into the capsid core. The consequence of this packing creates two pores on the capsid surface. The pore at the four-fold is approximately 4 to 5 Å across and predominantly hydrophobic, while the three-fold pore, being slightly larger at 6.0 Å diameter is predominantly hydrophilic. It is expected that one or both of these pores represent the point by which the hydrated iron diffuses into and out of the capsid.

In accordance with the invention, suitable proteins or peptides can be fused with the ferritin protein either as an exocapsid product by fusion with the N-terminal sequence lying adjacent to the capsid three-fold axis, as an endocapsid product by fusion with the C-terminus extending inside the capsid core, or a combination thereof. By ferritin is meant the ferritin protein and/or its H and/or L chains as well as ferritin analogs such as disclosed in U.S. Pat. No. 5,304,382, incorporated herein by reference, and apoferritin, as well as those proteins having the structure of ferritin, namely an outer surface having a N-terminal region and an inner core having an internal C-terminal region. The proteins or peptides useful in the invention will include those proteins, peptides, antibodies, fragments, enzymes, haptens, peptidoglycans or other molecules including amino acid sequences which can be linked to ferritin, and which can link to ferritin without disrupting its structure and which when expressed will form into a ferritin fusion protein which will self assemble into a large macromolecular or polymeric assembly, often pending the nature of the fusion products, with the same general physical structure and configuration (N terminal at the surface and C terminal in an inner core) as natural ferritin.

When designing the fusion product in accordance with the invention, it may be necessary to consider including 'spacer' residues, such as glycine or other suitable amino acids, between each ferritin and the protein or peptide fused to the ferritin. In general, a spacer will increase the distance between the center of the ferritin and the linked protein or peptide which may be desirable, e.g., in cases wherein it is desired to provide additional space between the ferritin portion of the fusion protein and the fused protein or peptide. This might arise in cases wherein the ferritin is fused to an antigenic protein or peptide and it is desired to have the antigen more exposed so as to raise antibodies such as in the case of vaccines. In addition, when the fusion protein of the invention is formed by a linking of ferritin with an antibody, a spacer may be desirable to allow the antibody to seek and bind with a target with less steric hindrance from the ferritin portion of the fusion protein. In general, the larger the linked molecule, the greater the need to have an adequate spacer. Accordingly, in the case of the fusion products of the invention, either endocapsid or exocapsid fusion product, one or more glycine (or other suitable amino acids) residues may be utilized if so desired to allow space for positioning of larger proteins around the exterior of the capsid. Glycine is generally desirable for this purpose since it can be used to create flexible 'tethers' which can also easily adapt to an extended polypeptide conformation.

As one skilled in the art would recognize, depending on the physiological or physical need, the desired protein or peptide may be fused inside the ferritin when it is desired to shield the protein from environmental factors which may, for example inactivate or otherwise cause degradation or cleavage, and may be fused outside the core when it is desired that the fused protein or peptide be unshielded such as when more rapid immunogenicity is desired. In addition, internal (C-terminal) or external (N-terminal) capsid fusion proteins may be used to form mixed capsids. For example, more than one antigenic protein or peptide can be expressed on the surface as well as within the core. This could be used to insure both antibody response as well as cellular immunity. Additionally, multiple enzymes expressed in the same manner can be used to create highly concentrated enzyme "factories" for multistep biochemical pathways. Such chimeric multivalent ferritins can be achieved through multiple expression in the same vector or by capsid dissociation by known methods and reassociation of the desired product as a mixture.

Figure 2A:
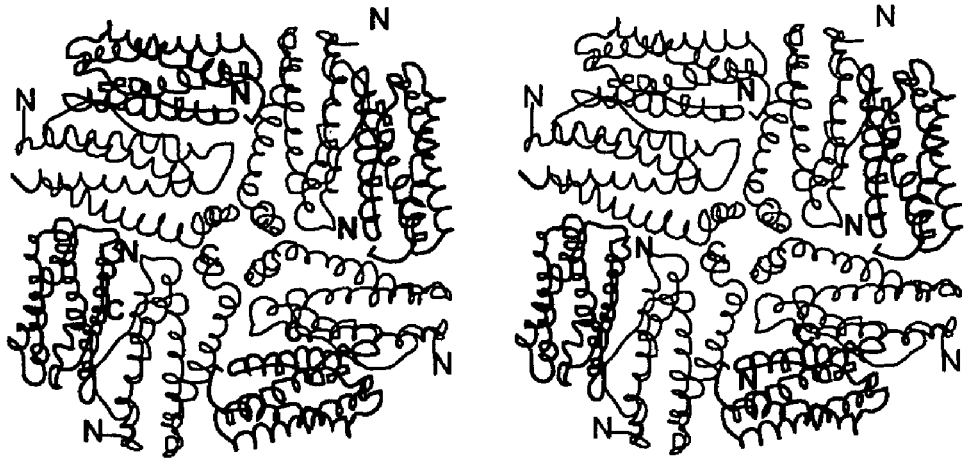
Figure 2B:
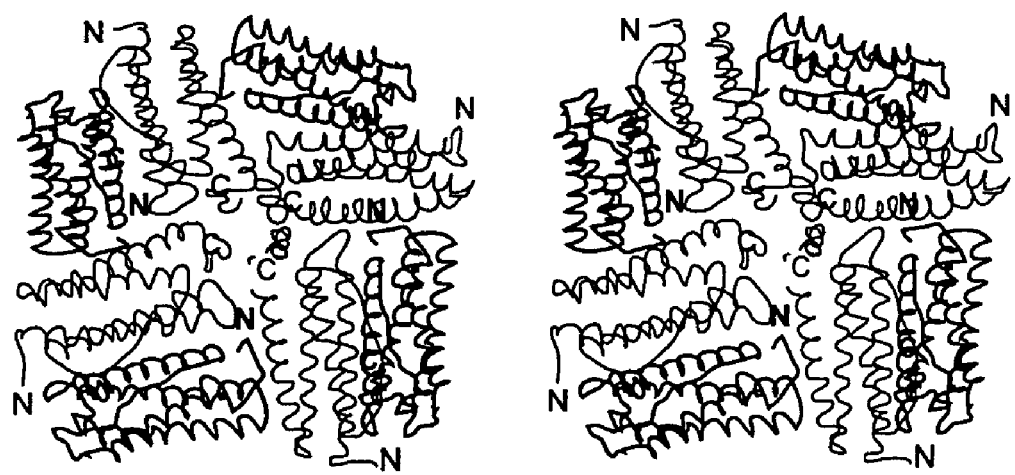

Accordingly, the present invention makes use of the placement of the N and C-termini at the outer and inner surface of the polymeric assembly respectively (FIGS. 2A & B), and allows for fusion proteins to be constructed using proteins or peptides linked to one or both of these sites. In the preferred embodiment, the ferritin fusion protein of the invention is prepared in any suitable manner wherein at least one protein or peptide can be linked to ferritin without causing a disruption of the resulting polymeric assembly, that is the protein or peptide and ferritin will stay linked while the fusion protein forms into the final stable polymeric assembly, and the ferritin will retain its basic structure of an inner core and an outer surface, with the linkage being either at the N terminal region at the outer ferritin surface or the C terminal region in the inner core of the ferritin (or at both regions if so desired). In one desired embodiment in accordance with the invention, the fusion protein will take on the polymeric capsid shape characteristic of ferritin. However, it is understood that the propensity of the ferritin to self associate can be advantageous and take on many different forms, and not just the capsid, and such forms may be other types of a polymeric assembly such as a polymeric aggregate, hemisphere, cylinder, etc. Self-assembly products which are formed in accordance with the invention by fusion with ferritin will still have desired properties for many applications, such as vaccines, as set forth further below. This fusion protein of the invention may be constructed using any suitable means that would be well known to one of ordinary skill in this art, such as recombinantly produced or produced under conditions wherein the individual protein units will form into the fusion protein of the invention, e.g., via chemical or physical means of fusion.

In accordance with the invention, the ferritin-fusion proteins will thus have expressed proteins which may be either incorporated onto the outer portion of the fusion protein, e.g., by linkage to the external N terminus, or which will be internalized through linkage with the C terminus. As set forth in more detail below, the functions of the protein fusion products in accordance with the invention include applications as vaccines, therapeutics, image contrast agents, novel metal chelating systems, gelling agents, protein purification platforms, therapeutic receptor-binding proteins, etc., and may be used in human and veterinary applications as well as numerous non-therapeutic applications.

Figure 3:
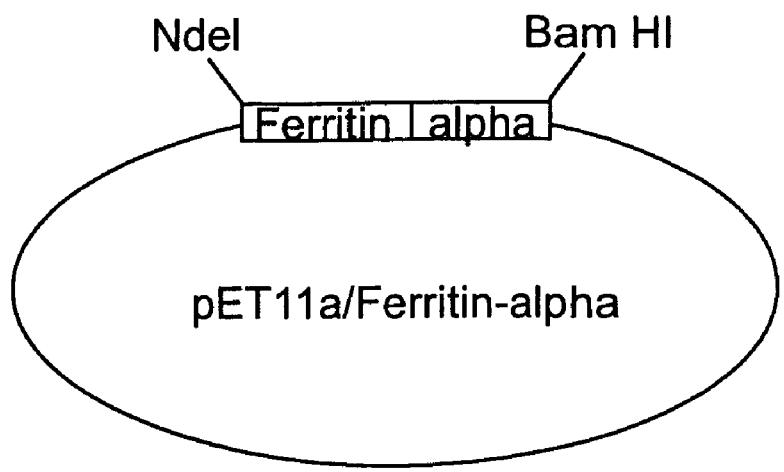
FIG. 3 is a schematic view of the plasmid coding for the fusion protein of human alpha chain hemoglobin to human ferritin C-terminus in accordance with the invention.

As indicated above, the recombinant production of the ferritin fusion proteins of the present invention can take place using any suitable conventional recombinant technology currently known in the field. For example, molecular cloning a fusion protein, such as ferritin with a suitable protein such as the recombinant human hemoglobin alpha subunit, can be carried out via expression in $E.\ coli$ with the suitable ferritin protein, such as the human ferritin L-chain. In this process, the full-length cDNA of Hemoglobin alpha was ligated to the C-terminal of ferritin light chain gene via a glycine linker (FIG. 3) using PCR-based methods. Following this preparation of the gene, protein expression and isolation and/or purification can be achieved, form example, by first verifying the coding sequence of the fusion protein (e.g., ferritin/hemoglobin) so that it has the correct DNA sequence. The construct may then be transformed into protein expression cells BL21 (DE3), grown to suitable size, e.g., OD 1.0 (600 nm) and induced at 30 degree with 1 mM of IPTG to activate T7 promoter. In this process, cells are resuspended in B-PER buffer and sonicated for protein release. The resulting fusion protein may be isolated and/or purified, such as from the supernatant using appropriate chromatographic or other methods, such as Size Exclusive and Gel Filtration Ion Exchange chromatography. The protein may be confirmed using conventional Western blot tests using suitable polyclonal and monoclonal antibodies.

Once the fusion proteins of the invention have been constructed it is possible to confirm capsid formation such as by the following observations:

1) the purified expression product eluted from size exclusion gel chromatography will have a retention factor consistent with a protein complex larger than native recombinant ferritin (ferritin MW, 408K);

2) light scattering experiments of the protein will show a monodispersed protein with an estimated diameter of approximately twice that of native ferritin (FIG. 6 and Table 2); and 3) Western blots using suitable polyclonal antibodies (e.g., in the specific case above, from both human ferritin and hemoglobin alpha) will each independently give positive results for the fusion product.

In accordance with the invention, the number of subunits in the fusion protein of the invention may be considerably greater in this complex than the 24 in native ferritin. This indicates that the capsid has an inherent ability to increase the angle of subunit-subunit packing and that dimers may rotate to pack with the 'B' helices parallel across the two-fold axis, and are potentially further stabilized through the flexibility of the 'Loop B-C' surface loops which pack as an antiparallel beta sheet across the two-fold axis. This hypothetical rotation could be encouraged by steric interactions, and thus a flattening of the capsid curvature would provide more accommodation of the large hemoglobin molecules. Small changes in these subunit packing angles could correlate with a great increase in capsid diameter and allow the incorporation of larger fusion products in the capsid core. It is further understood that the modification or replacement of the exposed surface loop, Loop BC, could also be used to create 'chimeric' ferritin molecules for vaccines and other applications.

The fusion proteins of the present invention may thus be utilized to enhance the properties of a number of proteins and peptides which are administered internally for a therapeutic purpose. In particular, through linkage with ferritin, the therapeutic protein will have its half life in plasma greatly extended when fused with ferritin which normally has a half-life of 18-20 hours. Thus, a beneficial protein or peptide will be able to continue providing therapeutic benefits long after the non-fused protein or peptide would have been completed degraded in the bloodstream. In addition, fusing the protein or peptide to ferritin may avoid immune related problems, especially in those cases wherein the fused protein is linked at the inner C-terminal region of ferritin. Similarly, the fusion to ferritin may also protect certain proteins and peptides (e.g., enzymes, toxic chelated compounds or small molecule therapeutics) which would otherwise be rapidly dissolved in the bloodstream, and once again in these cases it is desirable to have these peptides and proteins linked to the C-terminal region of ferritin so that they will fuse and be located in the inner encapsulated core of the ferritin portion of the fusion protein.

Economical and Scalable Isolation and Purification of Ferritin Fusion Products

Still further, by fusing a protein or small peptide with an incorporated enzyme cleavage site to the exterior of ferritin, the fusion product can be easily isolated once cleaved due to the large size difference of the ferritin capsid—simple ultrafiltration to isolate final product. Thus the ferritin fusion platform can be used for the convenient and inexpensive isolation of exocapsid fusion products.

Precipitation of Metal Complexes

The propensity of the ferritin core to precipitate a variety of metal complexes, including certain ceramics (see, e.g., U.S. Pat. Nos. 5,248,589; 5,358,722; and 5,304,382) in its natural state and given that novel metal nucleating peptides can be expressed in the core as illustrated in the enclosed Examples, it is understood that such metallic or inorganic complexes can be comprised of materials which promote the incorporation of radioactive elements, elements enhancing the properties of x-ray or nuclear magnetic resonance contrast agents, that are beneficial for a variety of medically related therapeutic, diagnostic, or prophylactic applications. It is further understood that by using the capsid architecture to advantage, precious or rare metals can be concentrated and precipitated in the core (as in the case of Fe normally) and as such these specialized ferritins can be used to easily isolate by means of fermentation processes with bacteria, yeast etc. expressing the protein desired or undesired inorganics. Recent interest has been in the control of particle size for nanoparticle production of semiconductor materials.

Antibody Directed Therapeutic Virus-Like Particles ("VLPs")

Exocapsid fusion products which are formed from a fragment (Fv) or greater domain structure of an antibody can direct therapeutics or diagnostics contained in the capsid or expressed on the surface, to specialized locations. In such an embodiment, it will be possible to link a protein or peptide containing an agent used to target or destroy cell such as tumors with a ferritin linked with an antibody (or an active region from an antibody such as an active fragment) which will allow the fusion protein to be directed to the target tissue (e.g., the tumor). Accordingly, in this manner capsids in accordance with the invention which contain toxic proteins, radioactive elements, or other destructive agents can be targeted directly to cancerous tissue.

Hemoglobin-Based Blood Substitutes

Ferritin fusion products with hemoglobin can potentially be used as novel blood substitutes. Potential advantages of such chimeric ferritins include 1) increased vasculature residence time; 2) restricted endothelial interaction limiting or eliminating the undesirable effect of binding nitrogen oxide; 3) encapsulated forms can protect hemoglobins from undesirable oxidation of Fe; and 4) polymeric forms can prevent dissociation of hemoglobin alpha chains from the beta chains.

Vaccines

The fusion proteins of the invention as described above, may also be utilized in the development of vaccines for active and passive immunization against infections, as described further below.

In a further embodiment, when linked to ferritin in a fusion protein in accordance with the invention, antibodies may be used as a passive vaccine which will be useful in providing suitable antibodies to treat or prevent infections.

As would be recognized by one skilled in this art, vaccines in accordance with the present invention may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of a fusion protein in accordance with the present invention is that amount which will be effective in immunizing a patient, i.e., in having that patient develop antibodies against a general or specific condition. This amount is generally referred to as an "immunogenic amount", and this amount will vary greatly depending on the nature of the antigen and of the immune system and the condition of the patient. Thus an "immunogenic amount" of fusion protein used in accordance with the active vaccines of the invention is intended to mean a nontoxic but sufficient amount of the antigenic agent such that the desired prophylactic or therapeutic generation of antibodies is produced. Accordingly, the exact amount of the immunogenic agent that is required will vary from subject to subject, depending on the species, age, and general condition of the subject, the severity of the condition being treated, the particular carrier or adjuvant being used and its mode of administration, and the like. Accordingly, the "immunogenic amount" of any particular fusion protein composition will vary based on the particular circumstances, and an appropriate immunogenic amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

Accordingly, an active vaccine in accordance with the invention is provided wherein an immunogenic amount of an isolated protein as described above is administered to a human or animal patient in need of such a vaccine. The vaccine may also comprise a suitable, pharmaceutically acceptable vehicle, excipient or carrier. In accordance with the invention, it is thus possible to link ferritin with viral proteins, e.g., envelope proteins or other proteins from such potentially highly pathogenic viruses such as AIDS, SARS, etc., and then use the fusion proteins as a means of developing antibodies against the AIDS and/or SARS viruses. In addition to providing vaccines which may be protective against such potentially deadly diseases, such fusion proteins may also be utilized in research concerning these diseases, and may be useful in developing methods or drugs in addition to vaccines which can be effective against these diseases.

When the fusion proteins of the invention are linked with antibodies, these may be used in passive vaccines. In this case, the preferred dose for administration of an antibody composition in accordance with the present invention is that amount will be effective in preventing of treating an infection, and one would readily recognize that this amount will vary greatly depending on the nature of the infection and the condition of a patient. An "effective amount" of fused antibody to be used in accordance with the invention is intended to mean a nontoxic but sufficient amount of the antibody such that the desired prophylactic or therapeutic effect is produced. Accordingly, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In addition, the antibody compositions of the present invention and the vaccines as described above may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

Another, functional aspect of the ferritin when compared to other virus capsid vaccines is that unlike a virus capsid which will be recognized by the immune system quickly, when an endocapsid fusion product in accordance with the present invention is used by itself, the capsid will not be recognized as foreign until is begins to disassemble and the antigen becomes exposed. That means that one could create a time-release antigenic effect which could potentially produce a greater immunity since exposure to the antigens will continue for a much longer period of time. The ferritin fusion proteins are less complicated and potentially much easier to make than virus-like ones, particularly those which have more than one protein structural component of the capsid.

Pharmaceutical Compositions

As would be recognized by one skilled in the art, the fusion proteins of the present invention may also be formed into suitable pharmaceutical compositions for administration to a human or animal patient in order to treat or prevent infections, or to be used as therapeutic agents against other diseases or conditions. Pharmaceutical compositions containing the fusion proteins of the present invention as defined and described above may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Other Applications

As set forth above, in accordance with the invention, the ferritin fusion proteins can have a number of potential uses in both the area of vaccines and other pharmaceutical and therapeutic compositions, as well as in many other areas which can provide beneficial effects. For example, the ferritin fusion proteins of the invention may be used to store radioactive metals in concentrated form which attached to antibodies can direct concentrated therapeutics to cancerous tissues. In addition, because of the potential ability of ferritin to bind iron and other precious metals, it may be possible to use the ferritin fusion proteins of the invention in systems wherein precious metals are obtained by scavenging methods, and this would provide an "Earth-friendly" mining operation since toxic chemicals could be avoided. In addition, since it appears that relative L and H chain composition may be involved in certain tissues, it is possible that ferritin fusion products having a specific proportion of L to H chains, or a predominant amount (e.g., 60-100%) of one type of chain may allow one to direct the capsids and therefore therapeutics (DNA, etc) to certain tissues. For example, it appears that heart muscle tissue generally is characterized by ferritins having predominantly H chains, wherein ferritin in the bloodstream is generally found to have predominantly L chains.

Still other applications include Macro structure assembly platform for more complicated systems—nano-technology applications. In addition, Ferritin, encapsulated therapeutics or other agents directed to therapeutic or other desired targets by attached antibodies or other means. In the case of antibodies, antibodies can be intact or possess only the antigen recognition portions, such as the Fv fragment and can be attached to ferritin by chemical or recombinant methods. It is also possible to modify through insertion various components of the ferritin capsid to produce hybrid molecules as vaccines and therapeutics. For example, the replacement of Loop BC located on the surface of the protein. It is also contemplated that certain difficult-to-crystallize peptides or proteins may be crystallized as the capsid—especially when expressed internally and thereby preserving the current exterior crystal packing interactions. Internal expression may also improve the solubility problems associated with certain hydrophobic proteins and peptides. The ferritin fusion proteins may also be used in applications wherein linkage will slow the rotation of a particle used in identifying processes such as NMR, image contrast, or X-ray imaging, and thus the fusion proteins of the invention will be useful in these contexts as well.

In short, the ferritin fusion proteins of the present invention as described above can be extremely useful in vaccines and other pharmaceutical and therapeutic compositions, and will have particular use in other applications such as drug delivery, oxygen transport, and other applications wherein enhancement of vascular residence time is desired.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Endocapsid Fusion

Recombinant Fusion of Human Alpha chain Hemoglobin to the Human Ferritin C-Terminus Via a Single Glycine Spacer Sequence.

Capsid Abbreviation: ($F_L$.G.Hα).

Molecular cloning: Recombinant human hemoglobin alpha subunit was expressed in *E. coli* as a human ferritin L-chain fusion protein. The full-length cDNA of Hemoglobin alpha was ligated to the C-terminus of ferritin light chain gene via a glycine linker (FIG. 3) using the PCR based method.

Protein expression and purification: Coding sequence of Ferritin/hemoglobin was verified by DNA sequence. The construct was transformed into protein expression cells BL21

(DE3). The transformed cells were grown to OD 1.0 (600 nm) and induced at 30 degree with 1 mM of IPTG to activate the T7 promoter. Cells were resuspended in B-PER buffer and sonicated for protein release. Recombinant fusion protein was purified from supernatant using Size Exclusive and Gel Filtration Ion Exchange chromatography. The protein was confirmed with Western blot using both polyclonal and monoclonal antibodies.

Capsid or self assembled particle (SAP) formation was indicated by the following observations:

1) the purified expression product eluted from size exclusion gel chromatography with a retention factor consistent with a protein complex larger than native recombinant ferritin (ferritin MW, 408K);

2) light scattering experiments of the protein shown in FIG. 5 & Table 1, indicated a monodispersed protein with an estimated diameter of approximately 2.5 times the size of native ferritin based on the values shown in FIG. 6 & Table 2 (these values are generally not accurate, but evidence for monodispersity are important in providing strong evidence for a uniform size and potentially ordered SAP); and 3) Western blots using polyclonal antibodies from both human ferritin and hemoglobin alpha each independently gave positive results for the fusion product.

Figure 4:
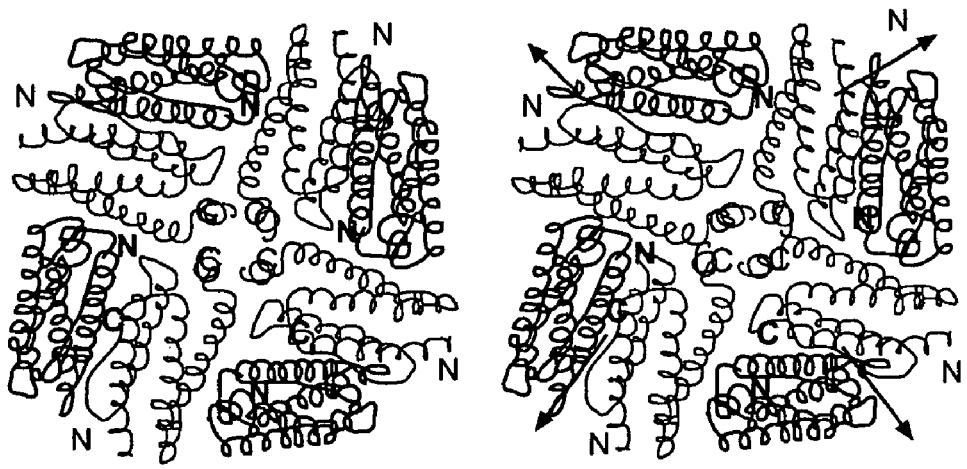
FIG. 4 is a stereo view of the packing around the 4-fold axis. The arrows indicate the direction of the hypothetical rotation of subunits to accommodate large C-terminal fusion products.

The number of subunits implied by the light scattering results is considerably greater in this complex than the 24 in native ferritin. While the exact configuration of the complex is currently unknown, the SAP is homogenous in nature consistent with a single molecular entity. These observations suggest that the subunit-subunit association has an inherent ability to increase the angle of packing. It is postulated that the dimers (shown in FIG. 4) rotate to pack with the 'B' helices parallel across the capsid two-fold axes, an interaction potentially further stabilized through the flexibility of the 'Loop B-C' surface loops which pack as an antiparallel beta sheet across the two-fold axes. This hypothetical rotation could be encouraged by the steric interactions between the hemoglobin alpha chain, i.e., a flattening of the capsid curvature would provide more accommodation of the large hemoglobin molecules. Small changes in these subunit packing angles could correlate with a great increase in capsid diameter and allow the incorporation of larger fusion products in the capsid core.

TABLE 1

Cumulants datalog of $F_L$.G.H$\alpha$. Data collected on a Proteinsolutions Dynapro light scattering spectrophotometer at 22 C.

| Meas. # | Time (s) | Amp | Diff | Rad (nm) | MW | Polyd. (nm) | Temp (C.) | Count Rate | Base Line | SOS |
|---|---|---|---|---|---|---|---|---|---|---|
| 1 | 10.00 | 0.5464 | 60.32 | 34.82 | 1.36E+04 | 23.52 | 20.0 | 1509998 | 1.0000 | 34.77 |
| 2 | 20.13 | 0.5379 | 61.50 | 34.15 | 1.30E+04 | 19.03 | 20.0 | 1557511 | 1.0000 | 24.08 |
| 3 | 30.26 | 0.5227 | 59.83 | 35.10 | 1.39E+04 | 21.33 | 20.0 | 1487880 | 0.9998 | 30.99 |
| 4 | 40.39 | 0.5142 | 61.69 | 34.04 | 1.29E+04 | 23.51 | 20.0 | 1558383 | 0.9974 | 27.37 |
| 5 | 50.53 | 0.5378 | 56.64 | 37.08 | 1.58E+04 | 26.54 | 20.0 | 1595309 | 0.9983 | 35.11 |
| 6 | 60.66 | 0.5393 | 60.72 | 34.59 | 1.34E+04 | 18.28 | 20.0 | 1498222 | 0.9998 | 18.44 |
| 7 | 70.79 | 0.5370 | 62.29 | 33.72 | 1.27E+04 | 24.31 | 20.0 | 1472016 | 1.0020 | 29.79 |
| 8 | 80.93 | 0.5499 | 58.83 | 35.70 | 1.45E+04 | 24.14 | 20.0 | 1566428 | 1.0030 | 30.84 |
| 9 | 91.06 | 0.5260 | 60.41 | 34.77 | 1.36E+04 | 19.45 | 20.0 | 1560468 | 0.9970 | 23.29 |
| 10 | 101.20 | 0.5329 | 60.25 | 34.86 | 1.37E+04 | 15.90 | 20.0 | 1573030 | 1.0020 | 32.37 |
| 11 | 111.30 | 0.5420 | 56.99 | 36.85 | 1.56E+04 | 26.87 | 20.0 | 1588833 | 0.9981 | 43.30 |
| 12 | 121.50 | 0.5432 | 58.73 | 35.76 | 1.45E+04 | 18.02 | 20.0 | 1582105 | 1.0010 | 29.54 |
| 13 | 131.60 | 0.5534 | 57.88 | 36.28 | 1.50E+04 | 23.24 | 20.0 | 1512688 | 0.9984 | 31.32 |
| 14 | 141.70 | 0.5516 | 60.52 | 34.70 | 1.35E+04 | 18.63 | 20.0 | 1492581 | 1.0060 | 34.87 |
| 15 | 151.90 | 0.5522 | 60.71 | 34.59 | 1.34E+04 | 18.58 | 20.0 | 1466885 | 1.0040 | 28.24 |
| 16 | 162.00 | 0.5625 | 59.91 | 35.05 | 1.39E+04 | 19.16 | 20.0 | 1513441 | 0.9983 | 28.34 |
| 17 | 172.10 | 0.5563 | 60.32 | 34.81 | 1.36E+04 | 16.63 | 20.0 | 1544321 | 0.9965 | 34.78 |
| 18 | 182.30 | 0.5470 | 56.92 | 36.89 | 1.56E+04 | 26.16 | 20.0 | 1595394 | 1.0000 | 39.68 |
| 19 | 192.40 | 0.5494 | 55.77 | 37.66 | 1.64E+04 | 24.23 | 20.0 | 1589674 | 1.0010 | 29.99 |
| 20 | 202.50 | 0.5540 | 60.85 | 34.52 | 1.34E+04 | 19.87 | 20.0 | 1538082 | 1.0020 | 19.80 |
| 21 | 212.70 | 0.5635 | 60.34 | 34.81 | 1.36E+04 | 18.32 | 20.0 | 1509841 | 1.0010 | 35.23 |
| 22 | 222.80 | 0.5771 | 58.34 | 36.00 | 1.47E+04 | 19.37 | 20.0 | 1535249 | 1.0020 | 32.82 |

TABLE 2

Cumulants datalog of native horse heart ferritin. Data collected on a Proteinsolutions Dynapro light scattering spectrophotometer at 22 C.

| Meas. # | Time (s) | Amp | Diff | Rad (nm) | MW | Polyd. (nm) | Temp (C.) | Count Rate | Base Line | SOS |
|---|---|---|---|---|---|---|---|---|---|---|
| 1 | 10.00 | 0.3740 | 163.3 | 12.86 | 1327 | 6.238 | 20.0 | 4462141 | 0.9999 | 13.34 |
| 2 | 20.14 | 0.3624 | 158.7 | 13.23 | 1417 | 8.482 | 20.0 | 4476535 | 0.9985 | 15.93 |
| 3 | 30.27 | 0.3517 | 159.2 | 13.20 | 1409 | 9.485 | 20.0 | 4438350 | 0.9987 | 14.73 |
| 4 | 40.40 | 0.3458 | 158.9 | 13.22 | 1415 | 5.018 | 20.0 | 4446134 | 1.0000 | 14.73 |
| 5 | 50.54 | 0.3486 | 158.7 | 13.23 | 1418 | 5.580 | 20.0 | 4412028 | 1.0010 | 12.01 |
| 6 | 60.67 | 0.3434 | 160.2 | 13.11 | 1387 | 7.886 | 20.0 | 4401034 | 0.9996 | 12.75 |
| 7 | 70.81 | 0.3440 | 157.6 | 13.33 | 1442 | 7.896 | 20.0 | 4413116 | 1.0000 | 12.36 |
| 8 | 80.94 | 0.3422 | 159.0 | 13.21 | 1412 | 4.990 | 20.0 | 4372660 | 0.9990 | 12.51 |
| 9 | 91.08 | 0.3455 | 155.8 | 13.48 | 1481 | 8.400 | 20.0 | 4376544 | 1.0010 | 13.24 |
| 10 | 101.20 | 0.3402 | 155.2 | 13.53 | 1494 | 7.226 | 20.0 | 4447649 | 1.0010 | 12.63 |
| 11 | 111.30 | 0.3392 | 155.3 | 13.53 | 1492 | 8.702 | 20.0 | 4496696 | 0.9995 | 13.41 |
| 12 | 121.50 | 0.3421 | 153.5 | 13.68 | 1533 | 8.607 | 20.0 | 4460202 | 0.9991 | 14.85 |
| 13 | 131.60 | 0.3426 | 153.7 | 13.66 | 1528 | 9.477 | 20.0 | 4415901 | 0.9997 | 14.45 |

TABLE 2-continued

Cumulants datalog of native horse heart ferritin. Data collected on a
Proteinsolutions Dynapro light scattering spectrophotometer at 22 C.

| Meas. # | Time (s) | Amp | Diff | Rad (nm) | MW | Polyd. (nm) | Temp (C.) | Count Rate | Base Line | SOS |
|---|---|---|---|---|---|---|---|---|---|---|
| 14 | 141.70 | 0.3368 | 156.2 | 13.44 | 1471 | 8.809 | 20.0 | 4380702 | 1.0000 | 18.02 |
| 15 | 151.90 | 0.3418 | 157.1 | 13.37 | 1453 | 6.909 | 20.0 | 4409014 | 0.9994 | 10.54 |
| 16 | 162.00 | 0.3406 | 155.0 | 13.55 | 1498 | 8.586 | 20.0 | 4369267 | 0.9998 | 11.70 |
| 17 | 172.10 | 0.3406 | 157.0 | 13.37 | 1453 | 7.102 | 20.0 | 4462261 | 0.9999 | 11.06 |
| 18 | 182.30 | 0.3416 | 155.3 | 13.53 | 1492 | 8.242 | 20.0 | 4390592 | 1.0010 | 12.73 |
| 19 | 192.40 | 0.3387 | 153.7 | 13.66 | 1528 | 8.784 | 20.0 | 4465543 | 1.0010 | 14.06 |
| 20 | 202.50 | 0.3386 | 156.3 | 13.44 | 1470 | 6.635 | 20.0 | 4451312 | 0.9998 | 10.17 |

Example 2

Endocapsid Fusion

Recombinant Fusion of Silver Condensing Peptide to the C-Terminus of Human L chain Ferritin Via a Two Glycine Spacer Sequence.

Capsid Abbreviation: ($F_L$.GG.Ag4), AG4 is NPSS-LFRYLPSD (Seq. ID No. 1)

The proper capsid formation, as an example of a metal scavenging peptide in combination with ferritin, was indicated by the following observations:

1) the purified expression product eluted from size exclusion gel chromatography with a retention factor consistent with the native recombinant ferritin (MW, 408K);

2) light scattering experiments of the protein shown in FIGS. 7 & Table 3 indicating a mono-dispersed protein with an estimated diameter of approximately 180 Å; 3) the silver condensing properties of the capsid were confirmed; and 4) TEM images indicated a polyhedral capsid with the proper external dimensions more consistent with the x-ray structure of ferritin (FIG. 8).

TABLE 3

Cumulants datalog of ($F_L$.GG.Ag4). Data collected on a
Proteinsolutions Dynapro light scattering spectrophotometer at 22 C.

| Meas. # | Time (s) | Amp | Diff | Rad (nm) | MW | Polyd. (nm) | Temp (C.) | Count Rate | Base Line | SOS |
|---|---|---|---|---|---|---|---|---|---|---|
| 1 | 10.00 | 0.3452 | 226.1 | 9.289 | 619.4 | 2.372 | 20.0 | 4053655 | 0.9998 | 2.853 |
| 2 | 20.14 | 0.3582 | 219.0 | 9.588 | 667.1 | 3.015 | 20.0 | 4093250 | 0.9997 | 2.641 |
| 3 | 30.27 | 0.3638 | 221.2 | 9.496 | 652.2 | 3.804 | 20.0 | 4065981 | 0.9992 | 3.905 |
| 4 | 40.40 | 0.3767 | 221.3 | 9.492 | 651.6 | 4.188 | 20.0 | 4055590 | 1.0000 | 4.852 |
| 5 | 50.54 | 0.4124 | 220.2 | 9.537 | 658.9 | 4.272 | 20.0 | 4039832 | 0.9996 | 7.010 |
| 6 | 60.67 | 0.4178 | 218.5 | 9.610 | 670.7 | 3.011 | 20.0 | 4095640 | 1.0010 | 5.197 |
| 7 | 70.80 | 0.4196 | 221.5 | 9.482 | 650.0 | 3.497 | 20.0 | 3961934 | 0.9998 | 5.097 |
| 8 | 80.94 | 0.4201 | 217.6 | 9.652 | 677.5 | 3.902 | 20.0 | 4038216 | 1.0000 | 4.480 |
| 9 | 91.07 | 0.4234 | 216.9 | 9.682 | 682.6 | 2.977 | 20.0 | 3996752 | 1.0000 | 5.728 |
| 10 | 101.20 | 0.4239 | 221.2 | 9.493 | 651.7 | 3.519 | 20.0 | 3967679 | 1.0000 | 3.414 |
| 11 | 111.30 | 0.4369 | 220.2 | 9.537 | 658.9 | 3.485 | 20.0 | 3942308 | 1.0000 | 3.742 |
| 12 | 121.50 | 0.4388 | 216.4 | 9.705 | 686.3 | 2.274 | 20.0 | 3923822 | 1.0000 | 4.641 |
| 13 | 131.60 | 0.4371 | 219.7 | 9.559 | 662.5 | 3.618 | 20.0 | 3928869 | 1.0010 | 4.548 |
| 14 | 141.70 | 0.4436 | 216.2 | 9.714 | 687.9 | 2.800 | 20.0 | 3998526 | 0.9994 | 5.508 |
| 15 | 151.90 | 0.4400 | 217.7 | 9.648 | 677.0 | 3.565 | 20.0 | 3961948 | 0.9995 | 3.895 |
| 16 | 162.00 | 0.4403 | 215.9 | 9.729 | 690.3 | 2.484 | 20.0 | 3973764 | 1.0000 | 5.826 |
| 17 | 172.10 | 0.4363 | 223.1 | 9.413 | 639.0 | 2.679 | 20.0 | 3928356 | 1.0000 | 4.784 |
| 18 | 182.30 | 0.4332 | 220.6 | 9.520 | 656.1 | 3.814 | 20.0 | 3978646 | 1.0000 | 4.470 |
| 19 | 192.40 | 0.4282 | 220.8 | 9.511 | 654.6 | 1.427 | 20.0 | 3999961 | 1.0000 | 2.819 |
| 20 | 202.50 | 0.4259 | 220.0 | 9.547 | 660.5 | 4.180 | 20.0 | 3994938 | 1.0010 | 4.707 |

Example 3

Exocapsid Fusion

Recombinant Fusion of HIV Tat Protein (84 mer) to the N-Terminus Via a Six (6) Glycine Spacer Sequence.
Capsid Abbreviation: (Tat.6G.$F_L$)
Where:
HIV Tat Sequence is

```
                                        (SEQ ID NO: 2)
MEPVDPRLEP WKHPGSQPKT ACTNCYCKKC CFHCQVCFIT

KALGISYGRK KRRQRRRAHQ NSQTHQASLS KQPTSQPRGD

PTGPKE -
```

Glycine Spacer is

```
GGGGGG (SEQ ID NO: 3)
```

Human ferritin L chain sequence is

```
                                        (SEQ ID NO: 4)
MSSQIRQNYS TDVEAAVNSL VNLYLQASYT YLSLGFYFDR

DDVALEGVSH FFRELAEEKR EGYERLLKMQ NQRGGRALFQ

DIKKPAEDEW GKTPDAMKAA MALEKKLNQA LLDLHALGSA

RTDPHLCDFL ETHFLDEEVK LIKKMGDHLT NLHRLGGPEA

GLGEYLFERL TLKHD
```

Molecular cloning: Recombinant wild type HIV-1 Tat was expressed in *E. coli* as a human ferritin L-chain fusion protein. The full-length cDNA of Tat was ligated to the N-terminus of the ferritin light chain gene with six Glycine linkers (FIG. 9) using the PCR based method.

Protein expression and purification: Coding sequence of Ferritin/Tat was verified by DNA sequence. The construct was transformed into protein expression cells BL21(DE3). The transformed cells were grown to OD 1.0 (600 nm) and induced at 30 degree with 1 mM of IPTG to activate T7 promoter. Cells were resuspended in B-PER buffer and sonicated for protein release. Recombinant fusion protein was purified from supernatant using Size Exclusive and Gel Filtration Ion Exchange chromatography. The protein was confirmed with Western blot using polyclonal and monoclonal antibodies (FIG. 10).

The proper capsid formation was indicated by the following observations:

1) the purified expression product eluted from size exclusion gel chromatography with a retention factor consistent with a protein on the order or larger than native recombinant ferritin (MW, 408K); 2) light scattering experiments of the protein shown in FIG. 11 & Table 4 indicating a mono-dispersed protein with an estimated diameter roughly twice that of native ferritin; and 3) Western blots using polyclonal antibodies to Tat gave positive results for the fusion product (FIG. 10).

TABLE 4

Cumulants datalog of (Tat.6G.$F_L$). Data collected on a Proteinsolutions Dynapro light scattering spectrophotometer at 22 C.

| Meas. # | Time (s) | Amp | Diff | Rad (nm) | MW | Polyd. (nm) | Temp (C.) | Count Rate | Base Line | SOS |
|---|---|---|---|---|---|---|---|---|---|---|
| 1 | 10.00 | 0.5372 | 64.68 | 32.47 | 1.16E+04 | 10.44 | 20.0 | 1056642 | 1.0030 | 10.32 |
| 2 | 20.14 | 0.5653 | 62.18 | 33.77 | 1.27E+04 | 11.77 | 20.0 | 1125065 | 0.9980 | 13.08 |
| 3 | 30.27 | 0.5784 | 61.52 | 34.14 | 1.30E+04 | 18.86 | 20.0 | 1111305 | 1.0000 | 20.11 |
| 4 | 40.40 | 0.5783 | 63.19 | 33.23 | 1.22E+04 | 15.06 | 20.0 | 1089854 | 0.9990 | 12.48 |
| 5 | 50.53 | 0.5717 | 64.18 | 32.72 | 1.18E+04 | 14.12 | 20.0 | 1095614 | 0.9972 | 10.08 |
| 6 | 60.67 | 0.5722 | 65.13 | 32.24 | 1.14E+04 | 7.92 | 20.0 | 1089823 | 0.9985 | 15.30 |
| 7 | 70.80 | 0.5740 | 64.68 | 32.47 | 1.16E+04 | 11.84 | 20.0 | 1089562 | 1.0010 | 9.33 |
| 8 | 80.93 | 0.5776 | 64.67 | 32.48 | 1.16E+04 | 14.45 | 20.0 | 1064212 | 1.0010 | 11.53 |
| 9 | 91.07 | 0.5833 | 63.48 | 33.08 | 1.21E+04 | 16.00 | 20.0 | 1087651 | 0.9993 | 16.48 |
| 10 | 101.20 | 0.5882 | 63.81 | 32.91 | 1.20E+04 | 15.88 | 20.0 | 1078616 | 0.9999 | 17.03 |
| 11 | 111.30 | 0.5846 | 63.55 | 33.05 | 1.21E+04 | 14.90 | 20.0 | 1059146 | 0.9973 | 15.79 |
| 12 | 121.50 | 0.6005 | 63.42 | 33.12 | 1.21E+04 | 14.67 | 20.0 | 1071728 | 0.9973 | 14.46 |
| 13 | 131.60 | 0.5982 | 62.87 | 33.40 | 1.24E+04 | 11.11 | 20.0 | 1112817 | 0.9993 | 9.72 |
| 14 | 141.70 | 0.6022 | 63.26 | 33.20 | 1.22E+04 | 10.18 | 20.0 | 1104251 | 1.0000 | 10.96 |
| 15 | 151.90 | 0.5945 | 65.18 | 32.22 | 1.14E+04 | 7.67 | 20.0 | 1113225 | 1.0020 | 5.47 |
| 16 | 162.00 | 0.5957 | 64.45 | 32.58 | 1.17E+04 | 11.57 | 20.0 | 1111261 | 1.0020 | 8.75 |
| 17 | 172.10 | 0.5880 | 64.25 | 32.69 | 1.18E+04 | 10.34 | 20.0 | 1124944 | 1.0000 | 15.35 |
| 18 | 182.30 | 0.6006 | 65.29 | 32.17 | 1.13E+04 | 7.27 | 20.0 | 1131531 | 0.9996 | 10.66 |
| 19 | 192.40 | 0.6046 | 64.26 | 32.68 | 1.18E+04 | 12.58 | 20.0 | 1097216 | 1.0000 | 14.31 |
| 20 | 202.60 | 0.6030 | 63.37 | 33.14 | 1.22E+04 | 13.85 | 20.0 | 1118774 | 1.0010 | 12.03 |

Example 4

Exocapsid Fusion

Recombinant Fusion of a Small HIV Tat Peptide to Human L Chain Ferritin with a Six (6) Glycine Spacer Sequence
Capsid Abbreviation: (TatP.6G.FL) where TatP is QPK-TACTNC (SEQ ID NO:5)

Molecular cloning: Recombinant wild type HIV-1 Tat peptide was expressed in *E. coli* as a human ferritin L-chain fusion protein. The full-length cDNA of Tat was ligated to the N-terminus of the ferritin light chain gene with six Glycine linkers (FIG. 12A) using a PCR based method.

Protein expression and purification: Coding sequence of Ferritin/Tat peptide was verified by DNA sequence. The construct was transformed into protein expression cells BL21 (DE3). The transformed cells were grown to OD 1.0 (600 nm) and induced at 30 degree with 1 mM of IPTG to activate T7 promoter. Cells were resuspended in B-PER buffer and sonicated for protein release. Recombinant fusion protein was purified from supernatant using Size Exclusive and Gel Filtration Ion Exchange chromatography. In this case the protein did not produce a positive Western blot using polyclonal and monoclonal antibodies, presumably due to the small size of the fusion peptide.

The proper capsid formation was indicated by the following observations:

1) the purified expression product eluted from size exclusion gel chromatography with a retention factor consistent with the native recombinant ferritin (MW, 408K).

Example 5

Exocapsid Fusion

Recombinant Fusion of HIV P24 Protein to the N-Terminus Via a Six (6) Glycine Spacer Sequence.

(P24.6G.F$_L$)

Molecular cloning: Recombinant wild type HIV-1 P24 was expressed in *E. coli* as a human ferritin L-chain fusion protein. The full-length cDNA of Tat was ligated to N-terminus of the ferritin light chain gene with six Glycine linkers (FIG. 12B) using the PCR based method.

Protein expression and purification: Coding sequence of Ferritin/P24 was verified by DNA sequence. The construct was transformed into protein expression cells BL21(DE3). The transformed cells were grown to OD 1.0 (600 nm) and induced at 30 degree with 1 mM of IPTG to activate T7 promoter. Cells were resuspended in B-PER buffer and sonicated for protein release. Recombinant fusion protein was purified from supernatant using Size Exclusive and Gel Filtration Ion Exchange chromatography. The protein may have a truncated P24 component (pending verification of expressed product). However, the resulting capsid fusion protein reacts to give a positive Western blot using polyclonal antibodies.

The proper capsid formation was indicated by the following observations:

1) the purified expression product eluted from size exclusion gel chromatography with a retention factor consistent with the native recombinant ferritin MW, 408K;

2) Protein fusion product reacts to give a positive Western Blot using polyclonal P24 antibodies.

APPENDIX TO EXAMPLES

1. GenBank Numbers:
   Human ferritin L chain: GenBank ID: M11147
   Human ferritin H chain: GenBank ID: AA075690
   Human hemoglobin alpha: GenBank ID: V00493
   HIV-1: GenBank ID: K03455

2. Amino Acid Sequences:

HIV-1 P24: PIVQNIQGQMVHQAISPRTL-NAWVKVVEEKAFSPEVIPMFSALSEGATPQDLNT MLNTVGGHQAAMQMLKETINEEAAEW-DRVHPVHAGPIAPGQMREPRGSDIAG TTSTLQEQIG-WMTNNPPIPVGEIYKRWI-ILGLNKIVRMYSPTSILDIRQGPKEPFR DYVDRFYKTLRAEQASQEVKN-WMTETLLVQNANPDCKTILKALGPAATLEEMM TAC-QGVGGPGHKARVL (SEQ ID NO: 6)

Tat-peptide: QPKTACTNC (SEQ ID NO: 5)

Alpha-globin: MVLSPADKTNVKAAWGKVGA-HAGEYGAEALERMFLSFPTTKTYFPHFDLSHG SAQVKGHGKKVADALTNAVAHVDDMP-NALSALSDLHAHKLRVDPVNFKLLSHC LLVT-LAAHLPAEFTPAVHASLDKFLASVSTVLTSKYR (SEQ ID NO: 7)

HIV Tat Sequence MEPVDPRLEP WKHPGSQPKT ACT-NCYCKKC CFHCQVCFIT KALGISYGRK KRRQR-RRAHQ NSQTHQASLS KQPTSQPRGDPTGPKE (SEQ ID NO: 2)

Human Ferritin L Chain Sequence MSSQIRQNYS TDVEAAVNSL VNLYLQASYT YLSLGFYFDR DDVA-LEGVSH FFRELAEEKR EGYERLLKMQ NQRG-GRALFQ DIKKPAEDEW GKTPDAMKAA MALEKKL-NQA LLDLHALGSA RTDPHLCDFL ETHFLDEEVK LIKKMGDHLT NLHRLGGPEA GLGEYLFERL TLKHD (SEQ ID NO: 4)

Human Ferritin H Chain Sequence MTTASTSQVR QNY-HQDSEAA INRQINLELY ASYVYLSMSY YFDRD-DVALK NFAKYFLHQSH EEREHAEKLM KLQNQRG-GRIFL QDIKKPDCDD WESGLNAMEC ALHLEKNVNQ SLLELHKLAT DKNDPHLCDF IETHYLNEQ VKAIKEL-GDH VTNLRKMGAP ESGLAEYLFD KHTWETVIMK AKPRANFP (SEQ ID NO: 8)

What is claimed is:

1. A ferritin fusion protein comprising a fusion protein selected from the group consisting of an L-chain ferritin protein fused at the C terminus with a protein or peptide capable of being fused to ferritin without interfering with the polymeric assembly of the resulting fusion protein and an L-chain ferritin protein fused at the N terminus with a protein or peptide capable of being fused to ferritin without interfering with the polymeric assembly of the resulting fusion protein,
wherein the protein is connected to ferritin by means of a spacer comprising at least one amino acid.

2. The ferritin fusion protein according to claim 1 wherein the fusion protein forms a polymer aggregate.

3. The ferritin fusion protein according to claim 1 wherein the fusion protein forms a capsid assembly.

4. The ferritin fusion protein according to claim 1 wherein the amino acid is glycine.

5. The ferritin fusion protein according to claim 4 wherein the glycine spacer has from one to six glycine units.

6. The ferritin fusion protein according to claim 1 wherein the protein fused to ferritin is selected from the group consisting of hemoglobin, silver condensing peptide, the HIV Tat protein, the small HIV Tat peptide, HIV-1 P24 protein, and viral proteins from the SARS or AIDS viruses.

7. The ferritin fusion protein according to claim 1 wherein the protein fused to ferritin is selected from the group consisting of SEQ ID NO: 1, SEQ ID NO:2, SEQ ID NO:5, SEQ ID NO:6 and SEQ ID NO: 7.

8. The ferritin fusion protein according to claim 1 that is prepared using recombinant means.

9. An immunogenic composition comprising an immunogenic amount of the fusion protein according to claim 1.

10. A composition comprising the fusion protein according to claim 1 and a pharmaceutically acceptable vehicle, carrier or excipient.

11. The composition according to claim 10 which is suitable for parenteral, oral, intranasal, subcutaneous, aerosolized or intravenous administration in a human or animal.

12. A method of eliciting an immunogenic reaction in a human or animal comprising administering to said human or animal an immunologically effective amount of an isolated fusion protein according to claim 1.

13. An isolated nucleic acid sequence coding for the fusion protein according to claim 1, or degenerates thereof.

14. A method of metal scavenging comprising introducing the fusion protein of claim 1 having a metal scavenging peptide fused to ferritin into a fluid containing the metals to be scavenged for a time sufficient to allow the metal to bond with the metal scavenging peptide of the fusion protein, and then recovering the fusion protein having the metal bound thereto.

15. A composition comprising an immunogenic amount of the fusion protein according to claim 1 and a pharmaceutically acceptable vehicle, carrier or excipient.

16. A ferritin fusion protein comprising a fusion protein selected from the group consisting of an L-chain ferritin protein fused at the C terminus with a protein or peptide capable of being fused to ferritin without interfering with the polymeric assembly of the resulting fusion protein and an L-chain ferritin protein fused at the N terminus with a protein or peptide capable of being fused to ferritin without interfering with the polymeric assembly of the resulting fusion protein,
    wherein the protein fused to ferritin is selected from the group consisting of hemoglobin, silver condensing peptide, the HIV Tat protein, the small HIV Tat peptide, HIV-1 P24 protein, and viral proteins from the SARS or MDS viruses.

17. A ferritin fusion protein comprising a fusion protein selected from the group consisting of an L-chain ferritin protein fused at the C terminus with a protein or peptide capable of being fused to ferritin without interfering with the polymeric assembly of the resulting fusion protein and an L-chain ferritin protein fused at the N terminus with a protein or peptide capable of being fused to ferritin without interfering with the polymeric assembly of the resulting fusion protein,
    wherein the protein fused to ferritin is selected from the group consisting of SEQ ID NO: 1, SEQ ID NO:2, SEQ ID NO:5, SEQ ID NO:6 and SEQ ID NO: 7.

18. A method of eliciting an immunogenic reaction in a human or animal comprising administering to said human or animal an immunologically effective amount of an isolated ferritin fusion protein, said ferritin fusion protein comprising a fusion protein selected from the group consisting of an L-chain ferritin protein fused at the C terminus with a protein or peptide capable of being fused to ferritin without interfering with the polymeric assembly of the resulting fusion protein and an L-chain ferritin protein fused at the N terminus with a protein or peptide capable of being fused to ferritin without interfering with the polymeric assembly of the resulting fusion protein.

19. A method of metal scavenging comprising:
    introducing a fusion protein having a metal scavenging peptide fused to ferritin into a fluid containing the metals to be scavenged for a time sufficient to allow the metal to bond with the metal scavenging peptide of the fusion protein, and then recovering the fusion protein having the metal bound thereto,
    wherein the fusion protein is selected from the group consisting of an L-chain ferritin protein fused at the C terminus with a protein or peptide capable of being fused to ferritin without interfering with the polymeric assembly of the resulting fusion protein and an L-chain ferritin protein fused at the N terminus with a protein or peptide capable of being fused to ferritin without interfering with the polymeric assembly of the resulting fusion protein.

\* \* \* \* \*

UNITED STATES PATENT AND TRADEMARK OFFICE
CERTIFICATE OF CORRECTION

PATENT NO. : 7,608,268 B2 Page 1 of 1
APPLICATION NO. : 11/374066
DATED : October 27, 2009
INVENTOR(S) : Carter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,608,268 B2 | Page 1 of 1 |
| APPLICATION NO. | : 11/374066 | |
| DATED | : October 27, 2009 | |
| INVENTOR(S) | : Carter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

In Column 27, Claim 16, line 37:

Please change "MDS viruses" to -- AIDS viruses --

Signed and Sealed this

Twenty-sixth Day of October, 2010

David J. Kappos
*Director of the United States Patent and Trademark Office*